(12) United States Patent
Welscher et al.

(10) Patent No.: US 10,881,292 B2
(45) Date of Patent: Jan. 5, 2021

(54) METHOD AND SYSTEM FOR DETERMINING THE REFRACTIVE PROPERTIES OF AN EYE OF A CHILD

(71) Applicant: Carl Zeiss Vision International GmbH, Aalen (DE)

(72) Inventors: Monique Welscher, Aalen (DE); Timo Kratzer, Aalen (DE)

(73) Assignee: Carl Zeiss Vision International GmbH, Aalen (DE)

(*) Notice: Subject to any disclaimer, the term of this patent is extended or adjusted under 35 U.S.C. 154(b) by 217 days.

(21) Appl. No.: 14/926,801

(22) Filed: Oct. 29, 2015

(65) Prior Publication Data
US 2016/0045107 A1 Feb. 18, 2016

Related U.S. Application Data

(63) Continuation of application No. PCT/EP2013/058928, filed on Apr. 29, 2013.

(51) Int. Cl.
*A61B 3/14* (2006.01)
*A61B 3/103* (2006.01)
(Continued)

(52) U.S. Cl.
CPC ............ *A61B 3/103* (2013.01); *A61B 3/0025* (2013.01); *A61B 3/0041* (2013.01);
(Continued)

(58) Field of Classification Search
CPC ... A61B 3/0025; A61B 3/0033; A61B 3/0083; A61B 3/0091; A61B 3/1015; A61B 3/103; A61B 3/111; A61B 3/145; A61B 3/032
(Continued)

(56) References Cited

U.S. PATENT DOCUMENTS

| 5,329,322 A | 7/1994 | Yancey |
| 5,790,235 A | 8/1998 | Kirschbaum |

(Continued)

FOREIGN PATENT DOCUMENTS

| CN | 2049519 U | 12/1989 |
| CN | 1095257 A | 11/1994 |

(Continued)

OTHER PUBLICATIONS

Written Opinion and International Search Report dated Jan. 20, 2014 in international patent application PCT/EP2013/058928 on which this application is based.

(Continued)

*Primary Examiner* — Mahidere S Sahle
(74) *Attorney, Agent, or Firm* — Walter Ottesen, P.A.

(57) ABSTRACT

The invention is directed to a system for determining the refractive properties of an eye. The system includes a wavefront measurement device for measuring the refractive properties of the eye. The system is configured to have at least one measurement mode assigned to children, wherein the system has an input device configured to switch the system into one of the at least one measurement mode assigned to children. The system is further configured to alter at least one of a group including a default pupillary distance, a default cornea vertex distance, a default position of the wavefront measurement device, a default position and/or direction of a measurement ray of the wavefront measurement device, a default position of a forehead and chin rest assembly of the system and a fixation target when the system is switched into the one of the at least one measurement mode assigned to children.

21 Claims, 11 Drawing Sheets

(51) Int. Cl.
*A61B 3/00* (2006.01)
*A61B 3/10* (2006.01)

(52) U.S. Cl.
CPC .......... *A61B 3/0075* (2013.01); *A61B 3/0083* (2013.01); *A61B 3/0091* (2013.01); *A61B 3/1015* (2013.01); *A61B 2503/06* (2013.01)

(58) Field of Classification Search
USPC .................... 351/204, 205, 211, 212, 246
See application file for complete search history.

(56) References Cited

U.S. PATENT DOCUMENTS

| | | | |
|---|---|---|---|
| 6,007,204 | A | 12/1999 | Fahrenkrug et al. |
| 6,382,795 | B1 | 5/2002 | Lai |
| 7,029,119 | B2 | 4/2006 | Youssefi et al. |
| 7,803,153 | B2 | 9/2010 | Thorn et al. |
| 7,806,529 | B2 | 10/2010 | Mihashi et al. |
| 8,419,185 | B2 | 4/2013 | Liang |
| 2002/0140902 | A1 | 10/2002 | Guirao et al. |
| 2003/0151721 | A1 | 8/2003 | Lai et al. |
| 2003/0163122 | A1 | 8/2003 | Sumiya |
| 2005/0105044 | A1 | 5/2005 | Warden et al. |
| 2005/0174535 | A1 | 8/2005 | Lai et al. |
| 2006/0203196 | A1* | 9/2006 | Van Heugten ......... A61B 3/103 351/221 |
| 2008/0291395 | A1* | 11/2008 | Dai ...................... A61B 3/0025 351/205 |
| 2008/0309882 | A1 | 12/2008 | Thorn et al. |
| 2009/0015787 | A1 | 1/2009 | Guillen et al. |
| 2009/0079937 | A1* | 3/2009 | Chen .................... A61B 3/0008 351/210 |
| 2013/0063699 | A1 | 3/2013 | Goldfain et al. |
| 2013/0286353 | A1* | 10/2013 | Steinmetz ............ A61B 3/0083 351/245 |
| 2014/0218681 | A1 | 8/2014 | Spratt et al. |
| 2014/0268056 | A1* | 9/2014 | Neal ...................... A61B 3/103 351/211 |

FOREIGN PATENT DOCUMENTS

| | | | |
|---|---|---|---|
| CN | 1781443 | A | 6/2006 |
| CN | 1889884 | A | 1/2007 |
| CN | 101224103 | A | 7/2008 |
| CN | 102334975 | A | 2/2012 |
| CN | 102641114 | A | 8/2012 |
| CN | 202458315 | U | 10/2012 |
| JP | H09215661 | A | 8/1997 |
| JP | 09234185 | A | 9/1997 |
| JP | H1156784 | A | 3/1999 |
| JP | H11104077 | A | 4/1999 |
| JP | 2005103069 | A * | 4/2005 |
| JP | 2005103069 | A | 4/2005 |
| JP | 2008246153 | A | 10/2008 |

OTHER PUBLICATIONS

English translation of an Examination Report of the Japanese Patent Office dated Nov. 15, 2016 in the rresponding Japanese patent application 2016-510942.
English translation of an Examination Report of the Japanese Patent Office dated Nov. 14, 2017 in the corresponding Japanese patent application 2017-025752.
Canadian search report of the Canadian patent office dated Oct. 24, 2017 in parallel Canadian patent application 2,910,379.
Translation and First Office action with Search Report of the Chinese Patent Office dated Mar. 9, 2017 in corresponding Chinese patent application 201380077897.1.
English translation and Third Office action of the Chinese Patent Office dated Mar. 30, 2018 in the corresponding Chinese patent application 201380077897.1.
Examination report No. 1 for standard patent application of the Australian patent office dated May 3, 2018 in parallel Australian patent application 2017235932.
English translation and Japanese Office action from the Japanese Patent Office dated Oct. 9, 2018 in rresponding Japanese patent application JP 2016-510942.
Office action from the European Patent Office dated Oct. 31, 2019 in corresponding European patent application 13 721 635.4-1124.
First office action from the Chinese Patent Office dated Mar. 31, 2020 in corresponding Chinese patent application 201810651048.7.
Zhangxing, Sheng, "Measurement of wave-front aberrations in the children's eyes using Asclepion shack-Hartmann aberrometer", Chinese Master's Theses Full-text Database, Medicine and Health Sciences, May 31, 2005, E073-16, 57 pages.
Extended search report from the European Patent Office dated Jul. 13, 2020 in corresponding European patent application 20161861.8-1122.

* cited by examiner

METHOD AND SYSTEM FOR DETERMINING THE REFRACTIVE PROPERTIES OF AN EYE OF A CHILD

CROSS-REFERENCE TO RELATED APPLICATION

This is a Continuation application of International patent application PCT/EP2013/058928, filed Apr. 29, 2013, the entire content of which is incorporated by reference.

BACKGROUND OF THE INVENTION

The current invention relates to a system for determining the refractive properties of an eye, the system comprising a wavefront measurement device for measuring the refractive properties of the eye. Further, the current invention relates to a method for determining the refractive properties of an eye, the method comprising the step of providing a system including a wavefront measurement device for measuring the refractive properties of the eye. In particular, the system and the method are related to determining the refractive properties of an eye of a child.

A method and a system for determining the refractive properties of an eye of a child are known from, for example, U.S. Pat. No. 5,329,322.

The vision-impaired human eye in general has refractive errors which in first approximation can be described in terms of a sphere, a cylinder and an axis orientation. This is based on the assumption that the eyesight defect can be approximately corrected through a lens with a toroidal surface. While it was customary in the past to determine the refractive errors of the human eye by relying on the subjective reaction of the person under examination when presenting to him a plurality of optotypes of different refractive power (subjective refraction), the possibility of measuring the refractive errors of the eye has now been available for several years (objective refraction). It is possible to measure the refractive power of the eye over the entire pupil and in particular also in the peripheral areas of the pupil. The measurable errors include for example spherical aberration, coma, trefoil error, higher orders of spherical aberration, et cetera. The objective refraction method is based on determining the wavefront of a propagating light bundle. The functional principal of a wavefront refractor is described in U.S. Pat. No. 6,382,795 B1, which also includes a synopsis of a plurality of different variants.

It has been customary for a few years to describe the refractive errors or imaging errors of the human eye by means of so-called Zernike polynomials. The errors of the eye near the center in regard to sphere, cylinder and axis can be described through second-order Zernike polynomials. These errors are therefore often referred to as second-order errors. The errors far from the center can be described through higher-order Zernike polynomials. These errors are therefore in general also referred to as higher-order errors. The information gained from a wavefront refractor can be used in the development of improved vision aids or improved eyesight correction methods. With vision aids such as for example a spectacle lens or a contact lens, correction of higher-order errors is possible at all or possible only under certain conditions. A spectacle lens has the peculiar property that the line of vision from the eye has to pass through different areas of the lens. Hence, a complete correction of higher-order errors in a spectacle lens is generally possible only for one specific direction of the line of vision. However, automatic wavefront measurement techniques can nevertheless lead to improved spectacle lenses and visual aids in general.

The subjective refraction is conventionally performed under daylight conditions with high-contrast optotypes. This leads to refraction values which are optimized for these conditions, that is, for a good illumination and for a high level of contrast. For many individuals, this method of refraction is not optimal for night vision or twilight vision. A wavefront measurement, on the other hand, can be performed in the dark or under mydriatic conditions. This provides the information for a much larger pupil, which opens the possibility to obtain an objective refraction result (in particular for a second-order refraction) which is also optimal for mesopic or scotopic light conditions. Spectacle lenses, in particular progressive lenses, can have intrinsic aberrations. These intrinsic aberrations can be combined with the wavefront measurement taken for the eye, as a means to compute and manufacture improved spectacle lenses.

The determination of a normal second-order and improved higher-order refraction resulting from the wavefront measurement is known from the prior art in a multitude of variations. A concept of deriving the second-order refraction from the averaged main curvatures of the wavefronts is disclosed in document U.S. Pat. No. 7,029,119 B1. A further apparatus and method for determining an eyeglass prescription for a vision defect of an eye is known from document United States patent application publication 2009/0015787 A1. Another system for determining a correction of aberrations in an eye of a person is described for example in document United States patent application publication 2002/0140902 A1. This system includes a computing device which allows the correction of the data signals to be determined in such a way that, if the correction is applied to the eye, an image quality metric in an image plane of the eye is objectively optimized. First, the computing device defines a search space (that is, values that can be assumed by the coefficients), which covers several sets of coefficients (for example, sphere, cylinder, axis, or the corresponding Zernike coefficients). Then, the previously selected image quality metric (for example, Strehl ratio, variance of point image washout function, energy of the point image washout function enclosed within the Airy disc, et cetera) is calculated for each of the sets of coefficients in the search space (that is, the corresponding dioptric values for defocus and astigmatism, as well as the associated axis orientation). Subsequently, the optimal value of the image quality metric is selected from all of the values of the image quality metric, and last, the correction is determined in conformance with one of the several sets of coefficients for which the optimal value of the image quality metric was calculated in the third step.

However, while the usage of objective refraction techniques is preferable, applying objective refraction techniques in the case of children has always been associated with problems as it is laid out in U.S. Pat. No. 5,329,322. Children have wide powers of accommodation and this means that conventional testing may obtain various refractive readings. Further, children simply do not stay in the same place for overlong periods of time. Finally, large and imposing optical apparatus—for example most conventional autorefractors—tend to excite and frighten the children. This is especially true if the intimate presence of an operator proximate the child person is required. Simply stated, an excited and frightened child falsely accommodates making the measurement of such refractions erroneous. Accommodative error is the biggest problem in providing accurate and reproducible measurements. In order to see objects close-up, the lens of the eye must change shape, become "fatter" so that the nearby object will be clearly focused on the retina. Looking into a box, or any type of instrument, even when the object being viewed inside the box is at optical infinity may induce accommodation. This is a predominantly psychological phenomenon. Even older children which are intelligent and try to cooperate may not be able to readily position themselves in the forehead and chin rests, because of lack of experience, properly fixate the target, and remain still for the requisite measurement time. For infants and younger children refraction at the age of less than six years is even more difficult.

All this makes the determination of the refractive properties of an eye of a child difficult. Hence, refractive errors in child's eyes often remain undetected or are detected relatively late. Further, determining the refractive properties with subjective refraction techniques usually does not apply to children as it is susceptible that they cooperate properly to successfully determine a reliable refraction via subjective refraction techniques.

Concerning objective refraction techniques, retinoscopy is used to determine the refractive properties of children's eyes in an objective manner. However, retinoscopy needs extensive skill to be properly conducted. Further, retinoscopy is extraordinarily time-consuming.

Hence, there remains a need for a quick and reliable technique to determine the refractive properties of an eye of a child.

SUMMARY OF THE INVENTION

In the current invention, a "child" is defined as a person of an age of ten or less years, in particular from and including three years to and including ten years. In particular, the current invention applies to pre-school children as with this age the problems outlined above are predominant.

According to one aspect of the invention, a system is provided for determining the refractive properties of an eye, the system comprising a wavefront measurement device for measuring the refractive properties of the eye, wherein the system is configured to have at least one measurement mode assigned to children, wherein the system has an input device configured to switch the system into one of the at least one measurement mode assigned to children, and wherein the system is further configured to alter at least one of a group consisting of a default pupillary distance, a default cornea vertex distance, a default position of the wavefront measurement device, a default position and/or direction of a measurement ray of the wavefront measurement device, a default position of a forehead and chin rest assembly of the system and a fixation target when the system is switched into the one of the at least one measurement mode assigned to children.

According to a further aspect of the invention, there is provided a system for determining the refractive properties of an eye, the system comprising a wavefront measurement device for measuring the refractive properties of the eye, wherein the system is configured to have at least one measurement mode assigned to children, wherein the system has an input device configured to switch the system into one of the at least one measurement mode assigned to children, and wherein the system is further configured to alter at least one of a group consisting of a default pupillary distance, a default cornea vertex distance, a default position of the wavefront measurement device, a default position and/or direction of a measurement ray of the wavefront measurement device and a default position of a forehead and chin rest assembly of the system, when the system is switched into the one of the at least one measurement mode assigned to children.

According to a further aspect of the invention, there is provided a system for determining the refractive properties of an eye, the system comprising a wavefront measurement device for measuring the refractive properties of the eye, wherein the system is configured to have at least one measurement mode assigned to children, wherein the system has an input device configured to switch the system into one of the at least one measurement mode assigned to children, and wherein the system is further configured to alter a fixation target, when the system is switched into the one of the at least one measurement mode assigned to children, wherein the system comprises a display device for displaying the fixation target, wherein the display device is configured to show a video comprising the fixation target, wherein the video is a series of images shown with a frequency of at least 20 images per second.

According to a further aspect of the invention, there is provided a method for determining the refractive properties of an eye, the method comprising the steps of:
 providing a system including a wavefront measurement device for measuring the refractive properties of the eye;
 switching the system into one of at least one measurement mode assigned to children;
 altering at least one of a group consisting of a default pupillary distance, a default cornea vertex distance, a default position of the wavefront measurement device, a default position and/or direction of a measurement ray of the wavefront measurement device, a default position of a forehead and chin rest assembly of the system and a fixation target; and,
 determining the refractive properties of the eye with the system.

According to a further aspect of the invention, there is provided a method for determining the refractive properties of an eye, the method comprising the steps of:
 providing a system including a wavefront measurement device for measuring the refractive properties of the eye;
 switching the system into one of at least one measurement mode assigned to children;
 altering at least one of a group consisting of a default pupillary distance, a default cornea vertex distance, a default position of the wavefront measurement device, a default position and/or direction of a measurement ray of the wavefront measurement device and a default position of a forehead and chin rest assembly of the system; and,
 determining the refractive properties of the eye with the system.

According to a further aspect of the invention, there is provided a method for determining the refractive properties of an eye, the method comprising the steps of:
 providing a system including a wavefront measurement device for measuring the refractive properties of the eye;
 switching the system into one of at least one measurement mode assigned to children;
 altering a fixation target; and,
 determining the refractive properties of the eye with the system, wherein the method further comprises showing a video comprising the fixation target, wherein the video is a series of images shown with a frequency of at least 20 images per second.

According to a further aspect of the invention, there is provided a, in particular non-transitory, computer program product comprising program code means for carrying out any of the above method or one of its embodiments, when the program code means are executed on a system for determining the refractive properties of an eye.

According to a further aspect of the invention, there is provided a non-transitory computer program product comprising program code means for carrying out a method comprising the steps of providing a system including a wavefront measurement device for measuring the refractive properties of the eye, switching the system into one of at least one measurement mode assigned to children, altering at least one of a group consisting of a default pupillary distance, a default cornea vertex distance, a default position of the wavefront measurement device, a default position and/or direction of a measurement ray of the wavefront measurement device, a default position of a forehead and chin rest assembly of the system and a fixation target, and determining the refractive properties of the eye with the system, when the program code means are executed on a system for determining the refractive properties of an eye.

In this context, the default pupillary distance and/or the default cornea vertex distance may be stored each as a parameter on a, in particular non-transitory, memory device of the system. Hence, the default cornea vertex distance may be a calculation parameter for determining a prescription or refraction for the person out of the determined refractive properties. Hence, the default pupillary distance may be a calculation parameter for determining the alteration of the position of the wavefront measurement device and/or the forehead and chin rest assembly.

The term "refraction" shall mean the optical correction needed to correct an ametropia of the person which ametropia is determined by the refractive properties of the eye of the person. The term "prescription" shall mean the determined properties of a spectacle lens, for example, in sphere, axis and cylinder, to provide the refraction as good as possible. Therefore, the system according to the current invention may further comprise a calculation engine or data processing unit for determining the refraction and/or the prescription.

According to a further aspect of the current invention, there is provided a method for determining a spectacle lens design for a child, the method comprising the step of determining the refractive properties of an eye of the child with a method according to any of the above aspects of the invention or one of its embodiments, the step of determining a refraction to correct an ametropia based on the determined refractive properties and the step of determining a spectacle lens design based on the refraction. Further, in a method for manufacturing a spectacle lens, a spectacle lens design may be acquired as outlined above and the further step of manufacturing the spectacle lens may then be conducted.

According to a further aspect of the invention, there is provided a method for determining a spectacle lens design for a child, the method comprising:
  determining the refractive properties of an eye using a method comprising the following steps:
    providing a system including a wavefront measurement device for measuring the refractive properties of the eye;
    switching the system into one of at least one measurement mode assigned to children;
    altering at least one of a group consisting of a default pupillary distance, a default cornea vertex distance, a default position of the wavefront measurement device, a default position and/or direction of a measurement ray of the wavefront measurement device, a default position of a forehead and chin rest assembly of the system and a fixation target; and,
    determining the refractive properties of the eye with the system;
  wherein the method for determining a spectacle lens design for a child further comprises:
    determining a refraction to correct an ametropia based on the determined refractive properties; and,
    determining a spectacle lens design based on the refraction.

In this, the term "spectacle lens design" means the configuration of the surface shapes of the front surface and/or the back surface of the spectacle lens.

According to a further aspect of the invention, there is provided a method for determining the refractive properties of an eye of a child, wherein the child is a person less than ten years old, in particular from three to ten years old, wherein the step of determining the refractive properties of the eye of the child is only based on a wavefront emanating from the eye. In particular, further, no subjective refraction is taken into account.

According to a further aspect of the invention, there is provided the use of a wavefront measuring device for determining an ametropic eye refraction of an eye of a child less than ten years old, in particular from three to ten years old.

According to a further aspect of the invention, there is provided a method for determining an ametropic eye refraction of an eye of a child less than ten years old, the method comprising the step of using a wavefront measuring device to determine the ametropic eye refraction of the eye of the child less than ten years old.

In particular, the refractive properties of the eye are determined via a wavefront measurement device for measuring the refractive properties of the eye. Further in particular, the wavefront measurement device is an aberrometer according to the Shack-Hartmann-principle, the Tscherning method or a ray-tracing method. However, any other type of wavefront sensor may also be used.

By this, there is provided the advantage that the refractive properties of the eye of a child can be determined reliably based only on an objective measurement technique. However, a measurement may take place in a quick manner. Usually, determining the refractive properties based on a wavefront emanating from the eye may take approximately thirty seconds. It has been found by the inventors that, contrary to prejudices present in the prior art, objective refraction techniques based on wavefront measurement devices can reliably be put into practice with young children. Therefore, measuring the refractive properties based on a wavefront emanating from the eye enables to completely replace the retinoscopy by fully automated wavefront measurement devices. This significantly facilitates the determination of the refractive properties of an eye and provides more reliable results as a basis for the treatment of refractive errors of children's eyes.

By this, a commonly known wavefront measurement device may be applied. However, via the input device, the measurement device can be set into at least one mode specifically for use with children. Thereby, certain hardware and/or software functionalities may be altered to fit to the specific needs for determining the refractive properties of an eye of a child, as explained in more detail below.

Further, the whole determination of the refractive properties is only conducted in an objective manner based on a wavefront emanating from the eye of the child, in particular a wavefront measurement device such as a Shack-Hartmann-sensor. This provides for the quickest and most reliable determination of the refractive properties. In particular, this enables the determination to be conducted in a fully automated manner that does not require any advanced skill on the side of the qualified person that conducts the tests, for example an optician.

The input device may be any kind of input device, for example a button or a keyboard or other device. Further, the input device may be a touch screen showing an icon to the user. By the selection of the icon, the system may then be set into the measurement mode assigned to children. In general, via the input device, it is possible to switch the system into a measurement mode specifically assigned to children. Further, it may be provided that an age of a person to be measured can be input into the system, for example via a keyboard or a touch screen. Depending on the age, for example in case the age is less than ten years, in particular from three to ten years, the system is switched into the measurement mode assigned to children. Of course, there may be more than one mode assigned to children. For example, there may be two modes, a first mode assigned to children of an age from and including three years to and including six years and a second mode assigned to children of an age from and including seven years to and including ten years.

The use of a wavefront measuring device for determining an ametropic eye refraction of an eye of a child less than ten years old, in particular from three to ten years old, has not been contemplated so far. For children, only retinoscopy has been established as a state of the art method for determining the refractive properties of an eye. It is a well established stereotype among opticians that in case of children retinoscopy is without any alternative. The inventors have found that this is actually not the case and that wavefront measurement devices may be used for children.

In an embodiment of the system, the system has a forehead and chin rest assembly, and the system is configured to move the forehead and chin rest assembly and/or the wavefront measurement device into an adjustment assigned to children upon switching the system into the one of the at least one measurement mode assigned to children, wherein the adjustment is based on an average eye-to-chin distance from and including 9.7 cm up to and including 10.7 cm. In particular, the average eye-to-chin distance is set to 10.2 cm, in particular wherein the eye-to-chin distance in particular is a vertical distance between a measurement ray, in particular a center of the measurement ray, of the wavefront measurement device and a chinrest, in particular of a chin resting surface of the chinrest, of the forehead and chin rest assembly.

In an embodiment of the method, the step of altering comprises moving a forehead and chin rest assembly of the system and/or a wavefront measurement device of the system into an adjustment assigned to children, wherein the adjustment is based on an average eye-to-chin distance from and including 9.7 cm up to and including 10.7 cm, in particular wherein the eye-to-chin distance in particular is a vertical distance between a measurement ray, in particular a center of the measurement ray, of the wavefront measurement device and a chinrest of the forehead and chin rest assembly.

The system may have a head and chin rest assembly and the system may be further configured to move the head and chin rest assembly into an adjustment assigned to children upon switching the system into the measurement mode assigned to children.

By this, it is possible to drive the head and chin rest assembly into a position that on average fits to the anatomics of a child. By this, the determination of the refractive properties can start quicker since the adjustment should already fit the child's anatomics on an average basis. In particular, the chin rest might be raised by a fixed amount, for example, by about 20 mm or by about 40 mm, relative to the height of the wavefront measurement device. Of course, manual refinement of the position and orientation of the head and chin rest assembly may be provided.

Alternatively or additionally, adapters for the chin and head rest may be provided that may be put on the respective parts of the conventional head and chin rest assembly. For example, in these adapter parts, the recess for the chin and the forehead may be formed to fit the anatomics of children. In particular, the children's anatomics are smaller than those of adults. Hence, in case a rest for the forehead and a rest for the chin are not movable relative to each other, the adapter parts may serve to fit a child's face into the forehead and chin rest assembly dimensioned for adults. For example, an adapter part may be placed on the chin rest that may have a thickness of about 10 mm to about 40 mm, in particular from an including 10 mm to and including 20 mm. In particular the thickness may be 10 mm, 20 mm, 30 mm or 40 mm. Further, an adapter part may be placed against the forehead rest that may have a thickness of about 1 mm to about 15 mm, in particular of about 5 mm to about 10 mm. In particular, the thickness may be 1 mm, 5 mm, 10 mm or 15 mm. The configuration of these adapter parts may be specifically suited for children, for example by their color and/or pictures on the adapter parts.

In an embodiment of the system, the system is configured to alter the default pupillary distance upon switching the system into the measurement mode assigned to children, wherein the default pupillary distance is set to a value in a range from and including 45 mm to and including 55 mm. In particular, the default pupillary distance is set to 48 mm or 54 mm. Further in particular, the default pupillary distance is set to 48 mm for children of an age from and including 3 years to and including 6 years and to 54 mm for children of an age from and including 7 years to and including 10 years.

In an embodiment of the system, the system is configured to alter the default cornea vertex distance to a value in range from and including 10.5 mm to and including 11.5 mm. In particular, the cornea vertex distance may be set to 11 mm. The system may be configured to alter the default cornea vertex distance upon switching the system into the measurement mode assigned to children, wherein the default cornea vertex distance is set to a value in a range from and including 10.5 mm to and including 11.5 mm.

Accordingly, in an embodiment of the method, the step of altering comprises setting the default pupillary distance to a value in a range from and including 45 mm to and including 55 mm, and/or in that the step of altering comprises setting the default cornea vertex distance to a value in range from and including 10.5 mm to and including 11.5 mm. Further in particular, the default pupillary distance is set to 48 mm for children of an age from and including 3 years to and including 6 years and to 54 mm for children of an age from and including 7 years to and including 10 years. In particular, the cornea vertex distance may be set to 11 mm.

The system may be configured to adjust a default pupillary distance into a pupillary distance assigned to children upon switching the system into the measurement mode assigned to children.

By this, the initial pupillary distance in the measurement mode assigned to children can already fit to the average children's eyes. This would facilitate and quicken the automatic capturing of the aperture of the pupil via image recognition. For example, the preset pupillary distance can be switched into a smaller initial condition as laid out above with reference to the position of wear parameters.

For adults, a standard configuration is usually adapted to average anatomical dimensions. Usually, a pupillary distance is predetermined to be 60, 64 or 68 mm for an adult. An average eye-to-chin distance predetermined for an adult is usually 11.4 cm. A predetermined cornea vertex distance for an adult is usually 12 mm. However, this might lead to a child's pupil not being within the range of a wavefront sensor in its initial default position and/or, in case of the cornea vertex distance, a prescription of the child not being properly suggested. Manually adjusting the system so that the child's pupil is within the range of the wavefront sensor and automatic capturing and adjusting procedures can be initialized may be cumbersome. Hence, by switching the default pupillary distance, the child's pupil would already be within range and automatic adjustment procedures can take place. The average pupillary distance at birth is approximately 42 mm and then grows by 1.6 mm for boys and 1.9 mm for girls. At the age of three, regardless of the gender, the average pupillary distance is 47 mm.

The system may be configured to adjust a default pupillary distance dependent on an age of the child, wherein the age is inputted into the system. The age might be inputted into the system manually. Further, the age might also be read out of data related to the child and stored in the system or transmitted to the system via a network. In particular, the default pupillary distance dependent on the age might be read out of a table stored in the system. Further in particular, the default pupillary distance might be calculated depending on a formula PD=42 mm+(age×1.9 mm) for boys and PD=42 mm+(age×1.6 mm) for girls, wherein PD is the default pupillary distance in Millimeters and "age" is the age of the child in years. Of course, corresponding method steps could also be conducted.

The system may be further configured to adjust a default cornea vertex distance into a cornea vertex distance assigned to children upon switching the system into the measurement mode assigned to children.

An average cornea vertex distance is set to be 12 mm for an adult. This is used when calculating a prescription, for example, sphere, cylinder and axis, out of the measured wavefront. Of course, the refractive properties of the spectacles to be prescribed depend on the assumed cornea vertex distance. Hence, in case of children, a different default cornea vertex distance is set. In particular, the default cornea vertex distance in the mode assigned to children is lower than the default cornea vertex distance for an adult. In particular, the default cornea vertex distance can be set to 11 mm.

In an embodiment of the system, the system is configured to alter the fixation target in the one of the at least one measurement mode assigned to children by at least one of a group consisting of choosing a type of the fixation target based on person's data, moving the fixation target on a display device of the system which display device is for displaying the fixation target and moving a display device of the system away from the eye which display device is for displaying the fixation target.

Accordingly, in an embodiment of the method, the system comprises a display device for displaying the fixation target, wherein the step of altering comprises at least one of a group consisting of choosing a type of the fixation target based on person's data, moving the fixation target on a display device of the system which display device is for displaying the fixation target and moving a display device of the system away from the eye which display device is for displaying the fixation target.

Hence, the system or the method may be configured to change the fixation target over time. By this, the attention and motivation of a child can be maintained. However, single fixation targets should not be too exciting as a static fixation on an exciting target may trigger an undesired accommodation of the child's eye. Hence, the fixation target may change with a certain time interval, for example a time interval in a range from and including every 1 second to and including every 12 seconds, in particular a time interval in a range from and including every 2 seconds to and including every 10 seconds, for example, a time interval in a range from and including every 3 seconds to and including every 7 seconds. For example, the time interval may be every two, five or ten seconds.

The system having the display device may be configured to fog the fixation target by moving the display device away from the eye. Such fogging of fixation targets may be used to further suppress a trigger for accommodation and is in general known to a person skilled in the art. For example, it may be provided to "fog" an eye of the person with a positive lens so that accommodation causes the fixated target to become more blurred. By this, the eye is encouraged to relax the accommodative mechanism. A fixation target such as a sailboat on the ocean, a tractor in a field, or a balloon in the sky, may be presented to the person. This fixation target may then be fogged to relax accommodation. Further, the system may be configured to choose a type of a fixation target based on person's data of the child. By this, person's data of the child stored for example in the system may be read out concerning, for example, the gender and/or age of the child. Based on this, a certain set of fixation targets may be chosen that are then provided to the child changing over time. In particular, there may be a set of fixation targets exclusively provided for boys and one exclusively provided for girls. As an alternative to the automatic setting of the fixation targets, it may also be possible that the system provides the possibility for a user input to choose the set of fixation targets manually.

In an embodiment of the system, the system comprises a display device for displaying the fixation target, wherein the display device is configured to show a video comprising the fixation target, wherein the video is a series of images shown with a frequency of at least 20 images per second.

Accordingly, in an embodiment of the method, the method further comprises showing a video comprising the fixation target, wherein the video is a series of images shown with a frequency of at least 20 images per second.

A video comprising a fixation target may be shown, wherein the video is a series of images shown with a frequency of at least 20 images per second. Preferably, the series of images is shown with at least 24 images per second. Even more preferably, the video is a series of images shown with a frequency of at least 30 images per second.

Hence, a video showing the fixation target to a person, in particular a child, more particular to a child of an age between three and ten years, may be shown. In this context, a video does not mean an arbitrary sequence of single images but a series of images shown with a frequency of at least 20 images per second. This is to ensure that a series of images is perceived as a movie by the person. By this, it is enabled that the video might comprise a moving fixation target. It has been found that moving fixation targets are advantageous to capture the attention of a person, in particular of child, during the wavefront measurement. Further, by this, and as will be described in the following in more detail, the video can be provided in a way that the fixation target moves to avoid accommodation by the eye. Hence, in particular in case of children, their attention can be captured and unwanted accommodation can be avoided, enabling pure objective refraction by wavefront measurement techniques with reliable results, even in the case of children.

In an embodiment of the system, the system further comprises an accommodation detection device, in particular a pupil size measurement device, and an alert device, wherein the system is configured to provide an alert with the alert device in case an accommodation is detected with the accommodation detection device, for example, the pupil size measurement device.

Accordingly, in an embodiment of the method, the method further comprises the steps of monitoring an accommodation of the eye, in particular with a pupil size measurement device, and providing an alert, in particular with an alert device, in case an accommodation is detected.

By this, in case of an accommodation being detected, an alert can be given that provides information if the measurement has to be conducted again. An example for a pupil size measurement device is, for example, given in document U.S. Pat. No. 5,790,235 A. Examples for an alert device may be an indication on a display of the system, a noise and/or any kind of visual indication, for example a lamp, on the system. In particular, the alert device may be used in case the diameter of the pupil decreases below a defined threshold. Further, an image processing device may also be provided, either hardware-implemented or software-implemented on a data processing unit, together with an image acquisition device, for example a camera, that acquires images of an eye and determines the pupil size, in particular its diameter, via image processing. For example, such an image processing could be an edge detection of the pupil's outer diameter. At the pupil's outer diameter there is an abrupt change from dark to bright. Hence, such an edge is readily detectable in image processing and generally known to a person skilled in the art. In particular, the devices may be the same as are being used to adjust the wavefront measuring device to the specific position of a pupil of a child at the beginning of the measurement process.

An accommodation of a pupil may be detected in case a diameter of the pupil reduces its size below a certain threshold. Such a threshold may be set as 50% of a largest diameter detected or as 70% of an initially detected diameter. Further, the system may be configured to track the size, in particular the diameter, of the pupil via the pupil measurement device continuously or in predefined time intervals, for example a time interval in range from and including 0.1 s to and including 1 s, in particular 0.1 s, 0.2 s, 0.5 s or 1 s, wherein s is the unit of seconds. By this, it is possible to track the pupil's size and a so-called "pumping" of the pupil, that is, the pupil's diameter increasing and decreasing alternately, may be detected. Such pumping of the pupil is also a strong indication for an unwanted accommodation.

In an embodiment of the system, the system is configured to show the fixation target moving from a first perceived distance to a second perceived distance, wherein the first perceived distance is smaller than the second perceived distance, wherein the first perceived distance is in a range from and including 1 diopters to and including 4 diopters, and wherein the second perceived distance is in a range from and including 0.5 diopters to and including 0 diopters.

Accordingly, in an embodiment of the method, the step of altering further comprises showing the fixation target moving from a first perceived distance to a second perceived distance, wherein the first perceived distance is smaller than the second per-ceived distance, wherein the first perceived distance is in a range from and including 1 diopter to and including 4 diopters, and wherein the second perceived distance is in a range from and including 0.5 diopters to and including 0 diopters.

In this, "diopters" means the unit of 1/m, wherein m is meters. Diopters is also abbreviated as "dpt". Hence, it is meant that in a "distance of 0 diopters" the human eye would need no extra accommodation to acquire a sharp picture, the eye would be focused to infinity. In, for example, a "distance of 3 diopters", the eye would need to accommodate for three more diopters to acquire a sharp picture. Hence, in case the fixation target is moved, for example, from "a distance of 3 diopters to a distance of 0 diopters" such an alteration of the fixation target relaxes the eye and helps to avoid accommodation.

Hence, the system having the display device may be configured to show a video as the fixation target. In particular, the video may comprise a fixation target shown in a perceived distance starting, for example, from 3 diopters and ending at 0 diopters. Instead of a static picture or a series of pictures, such a video might further contribute to avoiding accommodation and improve the child's attention. Hence, the child's viewing direction might be better focused on the target thereby improving the determination of the refractive properties.

It may be provided that the video comprises the fixation target being shown in different perceived distances. The term "perceived distance" in this context means that the actual distance of a display showing the video to a person, in particular a child, is not changed. However, the fixation target in the video changes its size in front of a background or in relation to other objects shown in the video, so that for the person, in particular the child, the fixation target appears to be farther away than before.

It has been found that the fixation target appearing to move farther away from the person in the video shown to the person leads to the eye and its pupil turning into a relaxed state. Hence, accommodation can be avoided and the pupil may remain opened. Further, a moving fixation target helps to catch and maintain the attention of a person, in particular a child, in particular a child of an age from three to ten years.

The video may comprise the fixation target being shown moving from a first perceived distance to a second perceived distance, wherein the first perceived distance is smaller than the second perceived distance. In other words, in the perception of the person, in particular a child, the fixation target moves away from the person. As already explained such a fixation target helps to relax the person's eye and may help to avoid accommodation.

In a further embodiment of the system or the method, the video may comprise the fixation target being shown moving from a third perceived distance to the first perceived distance, wherein the third perceived distance is larger than the first perceived distance.

In other words, the fixation target moves, in the person's perception, towards the person during the video being shown. The third perceived distance may be equal to the second perceived distance or may be different from the second perceived distance. Particularly, there will be provided that the fixation target moves from the third perceived distance to the first perceived distance prior to moving from the first perceived distance to the second perceived distance. Hence, it may also be provided that the fixation target first moves towards the person and then moves away from the person, in particular fades away into infinity. This may further avoid accommodation during the time when the fixation target moves away from the person, in particular the child. Hence, it may be provided that the wavefront emanating from the eye is measured during a time interval in which the fixation target moves from the first perceived distance to the second perceived distance.

In a further embodiment of the system or the method, it may be provided that the video is shown on a display, wherein an actual distance between the display and the eye is altered when the video is shown, in particular wherein the display is moving away from the eye when the video is shown.

Hence, it may also be provided for a fogging of the fixation target, in articular as may be done by moving the display away from the person. This may support to avoid accommodation. In particular, the actual distance between the display and the eye may be altered during the time of the video being shown, in particular during the time when the fixation target is being shown moving from the first perceived distance to the second perceived distance.

In a further embodiment, the method may comprise the step of playing an audio content when the video is shown.

Hence, the system correspondingly provided may comprise a speaker system to play sound to the person, in particular the child. The audio content may be a melody or music to set the person, in particular the child, into a relaxed mood. It has been shown that such influences may help avoiding the accommodation of an eye. Further, it may be provided that the audio content is a sound corresponding to the video shown on the display. Hence, the audio content may comprise voice info and other sounds of objects, cartoon figures and persons shown in the video.

In general, the system may be further configured in that upon starting the measurement mode assigned to children, a cartoon figure is shown to the child via the display device that explains the measurement to the child. Further, in this kind of instruction video, it may be explained to the child what is important and how the child may support the measurement to achieve good results.

In general, the switching of the system into a measurement mode assigned to children may be conducted by any kind of input device. The input device may be a certain button provided on the system. Further, the input device may be a keyboard or track ball or mouse device that enables clicking a certain button on a display of the system. Of course, also a voice command may be implemented that enables switching the system into the measurement mode assigned to children via a single voice command. Hence, the input device may also be a microphone device with voice detection.

Of course, the features explained above and explained in the following description may not only be used in the specific combinations given but also independently or in any other combination of the disclosed features without departing from the scope of the invention.

BRIEF DESCRIPTION OF THE DRAWINGS

The invention will now be described with reference to the drawings wherein.

DESCRIPTION OF THE PREFERRED
EMBODIMENTS OF THE INVENTION

Figure 1:
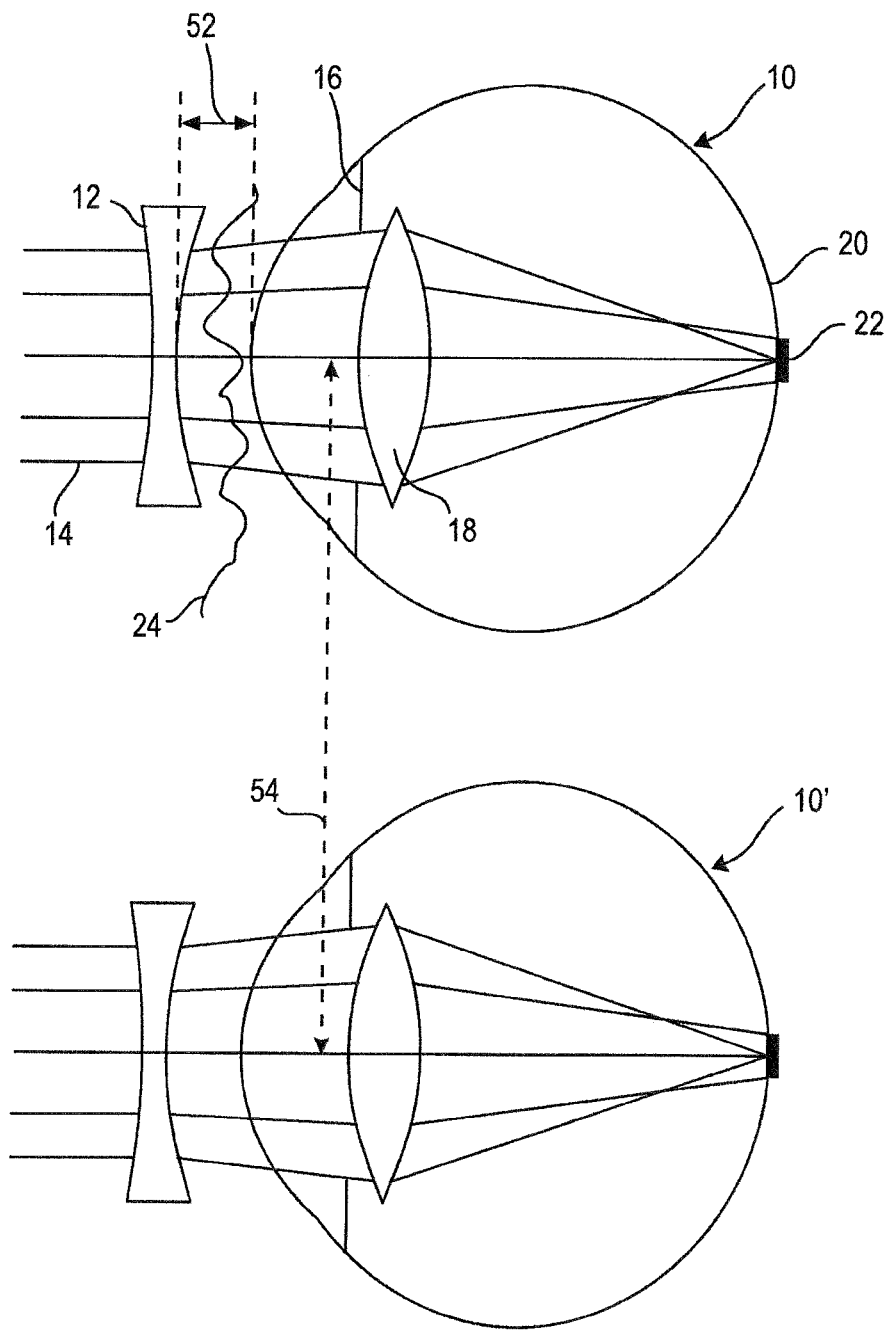
FIG. 1 shows a schematic of an eye in a pair of eyes.

In FIG. 1, a schematic illustration of an eye 10 is shown. The eye 10 may be considered as the eye of a child to be measured and, in case of a refractive error, being corrected. Shown is also a lens 12 of a spectacle. The lens 12 is used to correct for errors of the eye 10. By this, it is possible that rays of light 14 may travel through the lens 12 and the eye 10 without any refractive errors. An iris 16 is schematically illustrated through which the rays of light 14 may pass. They then travel through the eye lens 18 and are focused on a certain part 22 of the retina 20. Hence, only a fully-opened pupil provides that all parts of the eye lens 18 and, hence, all refractive errors can be recognized when the refractive properties of the eye 10 are measured. Then, a wave front 24 comprising the whole bundle of light rays passing through the open pupil of the iris 16 can be measured.

In FIG. 1, further, a second eye 10' is shown to visualize some of the parameters that may be altered according to the system and method as will be described in further detail below. In FIG. 1, a cornea vertex distance 52 is designated. This is the difference between the backside of the lens 12 and the cornea of the eye 10. Further, a pupillary distance is designated with the reference numeral 54 which is the distance between the center of the pupils of the two eyes 10 and 10'.

Figure 2:
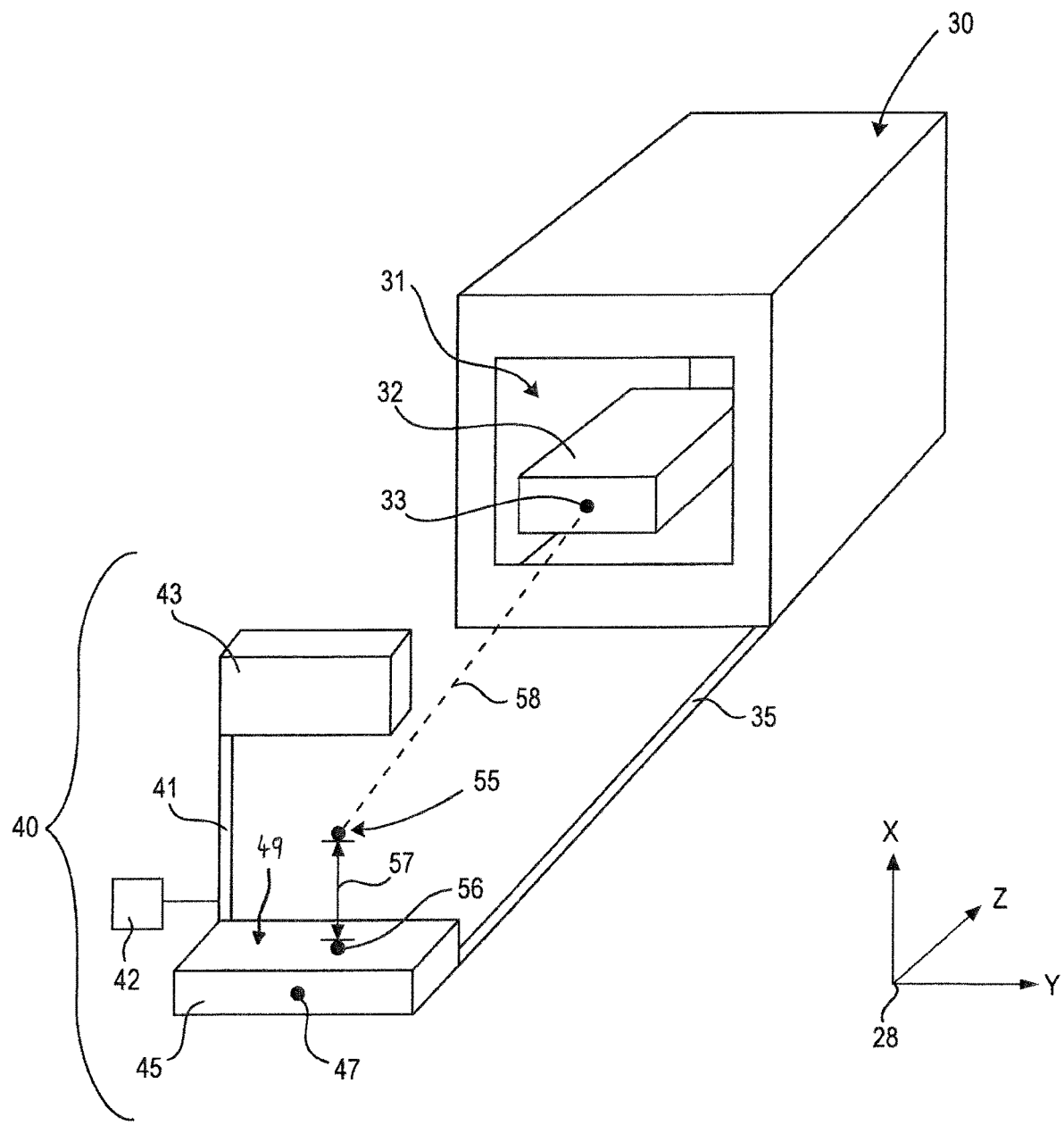
FIG. 2 shows an embodiment of a system for determining the refractive properties of an eye.

In FIG. 2, a system 30 according to an embodiment is shown. The schematic illustration shows the system 30 having a wavefront measurement device 32. The system 30 is provided with an opening 31 through which the wavefront measurement device 32 may measure the refraction of an eye 10 of a person. The position of the wavefront measurement device is designated with reference numeral 33. The position of the wavefront measurement device 32 within the system 30 may be adjustable. Hence, the wavefront measurement device 32 may be moved. A coordinate system X, Y, Z is designated with reference numeral 28. In the schematic shown in FIG. 2, the wavefront measurement device 32 may in particular be movable along the X-axis. Further, it may be provided that the wavefront measurement device 32 may be swiveled at least around the X-axis (vertical axis), but optionally also around the Y-axis (horizontal axis) and/or the Z-axis, to be aligned towards a particular eye of the person.

The system 30 has a head and chin rest connection 35 by which a head and chin rest assembly 40 is attached. The head and chin rest assembly 40 has a head rest 43 against which a forehead of a person is to be positioned and, further, has a chin rest 45 on which a chin of the person is to be positioned on a chin resting surface 49. The head rest 43 and the chin rest 45 may be connected via a connection device 41 and may be movable relative to each other via an actuation unit 42. By this, a height of the chin rest 47 along the X-direction may be adjustable. Further, the height of the overall head and chin rest assembly 40 may be adjustable along the X-direction, for example via a further actuation unit (not shown). By this, it may be possible to adjust a position 47 of the chin rest 45 along the X-direction and, hence relative to the head rest 43 and relative to the height of the wavefront measurement device 32 and, therefore, the position 33 of the wavefront measurement device 32. As a default chin position 56 on the chin resting surface 49 of the chin rest 45 is known, it is possible—based on an average eye-chin-distance 57—to assume the default eye position 55. The eye-chin-distance is the vertical (X) distance between a measurement ray 58, in particular the center of the measurement ray 58, of the wavefront measurement device 32 and a chin rest 45 of the forehead and chin rest assembly 40, in particular the chin resting surface 49 of the chin rest 45. This may further take into account the default pupillary distance 54. By this, based on these default eye positions, it is possible to adjust the measurement ray 58 of the wavefront measurement device 32 initially in a way that it already closely matches the actual eye position. This avoids cumbersome manual adjustment procedures.

Further, the store parameter of the cornea vertex distance 52 set per default in the wavefront measurement device 32 may be adjusted so that a prescription suggested based on the wavefront measurement results best fits the average need of a child. In particular, the wavefront measurement device 32 may have at least one, preferably more than one, measurement mode assigned to children in which at least one of the parameters set above is initially altered towards a value assigned to children. In particular, this may take place according to the following

TABLE 1

| | default PD [mm] | average eye-chin distance [cm] | default CVD [mm] |
|---|---|---|---|
| Child (3-6 J) | 48 | 10.2 | 11 |
| Child (7-10 J) | 54 | | |
| Adult | 64 | 11.4 | 12 |

Figure 3:
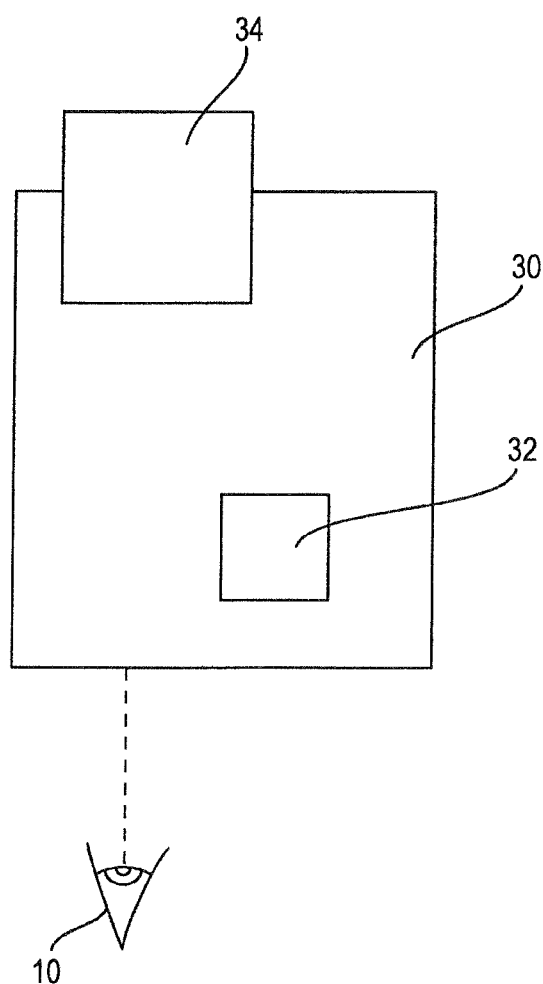
FIG. 3 shows a further embodiment of a system for determining the refractive properties of an eye.

FIG. 3 shows an embodiment of a system 30 for determining the refractive properties of an eye of a child. The system 30 comprises a wave front measuring device 32, for example a Shack-Hartmann-sensor. Further, the system comprises an input device 34. Via the input device 34, which may be any kind of input device, for example a button or a keyboard or other device, it is possible to switch the system 30 into a measurement mode specifically assigned to children. Further, the system 30 may comprise a display that shows the measurement mode the system 30 is switched into. Of course, this may also be shown via lamps or other visual indicators. By this, it is possible to measure the eye 10 of a child with an objective refraction technique that measures a wave front over the whole pupil of the child. This is not only quicker than commonly known refraction techniques for children but also provides wave front aberrations over the whole pupil diameter.

Figure 4:
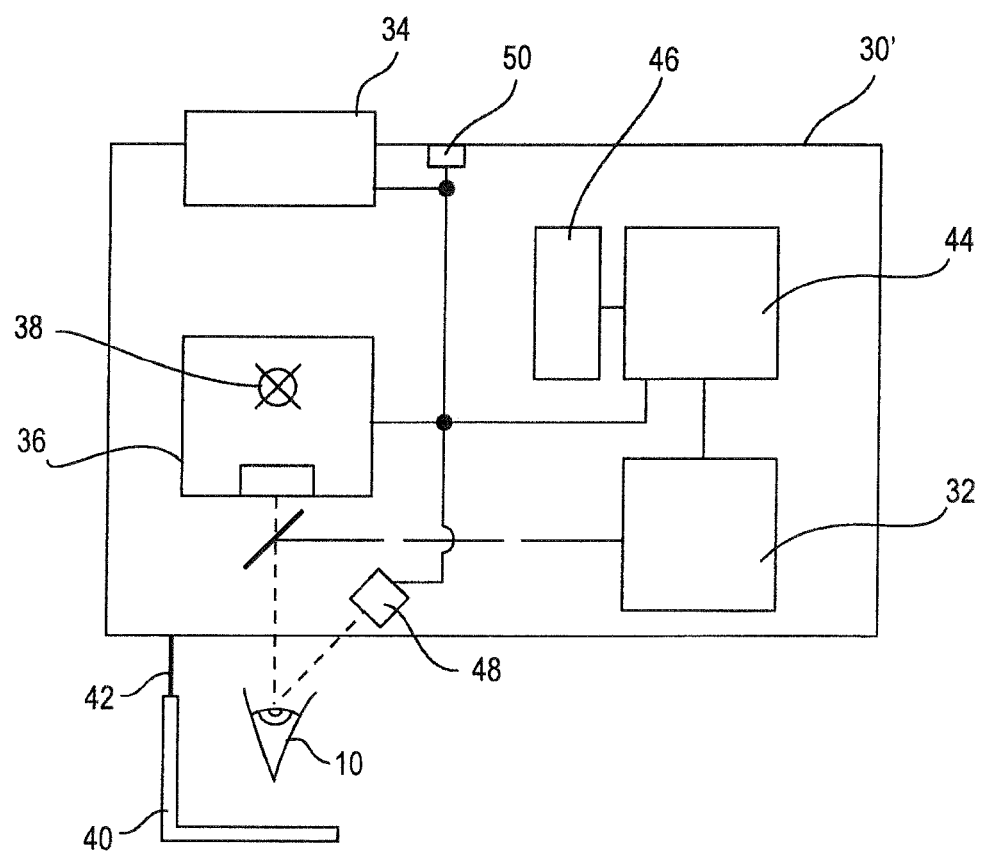
FIG. 4 shows a further embodiment of a system for determining the refractive properties of an eye.

FIG. 4 shows a further embodiment of the system 30'. In this embodiment again, a wave front measurement device, for example a Shack-Hartmann-sensor, 32 is present. Further, the input device 34 is provided. Even further, the system 30 has a display device 36, for example any light-emitting device that may project a fixation target 38 into the eye 10 of the child. Also, the display device 36 may be embodied by any kind of display that shows certain fixation targets 38 to the child. The system 30' further comprises a head and chin rest assembly 40 that is connected via a properly configured actuation unit 42 to the system 30. By this, the head and chin rest assembly 40 can be controlled and moved in a proper position so that the forehead and the chin of a child may rest on it. In particular, in case the system 30' is switched via the input device 34 into a measurement mode assigned to children, an initial position for children can automatically be set for the head and chin rest assembly 40.

The system 30' may further comprise a central processing unit 44 that controls the system 30'. A memory unit 46 may be in connection to the central processing unit 44. The central processing unit 44 may control the whole system, for example the display device 36, the wave front measurement device 32 and the input device 34. Further, a pupil size measurement device 48 may be present that is also controlled via the central processing unit 44. Further, the central processing unit 44 may collect all data required via the wave front measurement device 32, the pupil size measurement device 48 and the input device 34. The central processing unit 44 may be properly configured so that it is able to determine a prescription based on the measurement results or any higher order refraction. Further, the central processing unit 44 may even be configured such that it is able to determine a corresponding lens configuration. However, the central processing unit 44 may also be connected via a data network (not shown) to other data processing units either in a wired or wireless manner. The further data processing units may also be situated at different sites as will be explained in further detail below.

A central processing unit 44 may control the display device 36 to provide a specific series of fixation targets 38 to a child. The kind of set of fixation targets 38 may be read out of a memory unit 46 based on person's data that may be also present in the memory unit 46 or input via the input device 34. Of course, the set of fixation targets 38 may also be chosen via the input device 34. Of course, there may also be a video shown to a child via the display device 36 as a fixation target. Further, it may be the case that upon a start of the measurement process, some kind of animation is provided to the child that explains the whole measurement and how the child should behave in order to provide good results. In general, the fixation target 38 is chosen in a way that it catches the attention of the child without exciting it too much as this might cause an undesired accommodation.

Further, the system 30' may comprise an alert device 50, for example a light or a sound device. Of course, in case the system 30' comprises a display, the alert device 50 may also be formed as a corresponding indication on the display (not shown). Hence, in case the pupil diameter of the eye 10 should fall below a certain threshold, the pupil diameter acquired via the pupil size measurement device 48 and optionally forwarded, for example, to the central processing unit may cause the alert device 50 to provide an alert. By this, a corresponding measurement may automatically be discarded and a further measurement process may be started.

Figure 5:
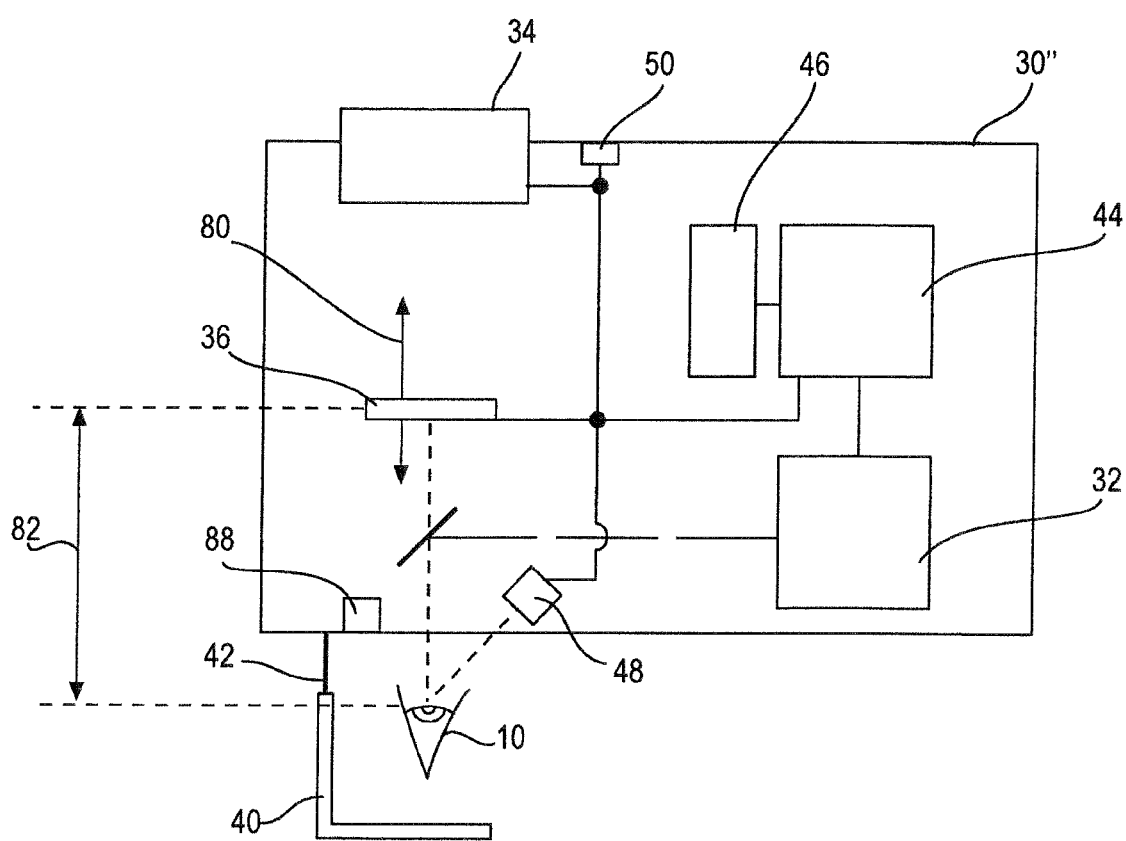
FIG. 5 shows another embodiment of a system for determining the refractive properties of an eye.

FIG. 5 shows a further embodiment of the system 30". Like elements as in FIG. 4 are designated with like references and will not be explained again. In the embodiment shown in FIG. 5, the display device 36 is provided as a display or screen, which may, for example, be a display based on an LCD (liquid crystal display) technique or on LED (light-emitting diode) display techniques. In other words, the display device 36 shown in FIG. 5 is an analogue display device or a digital display device, for example an array of light-emitting elements, able to be controlled by the central processing unit 44 to display a video to the eye 10. The video shows the fixation target 38 to the eye. Hence, the fixation target 38 may move on the display, change its size and so on. An actual distance 82 between the display 36 and the eye 10 may be altered by moving the display 36 farther away or towards the eye 10, as indicated by the arrow 80. Hence, while the fixation target 38 may not change its size in the video, by altering the actual distance 82 it may nonetheless appear closer or farther away from the eye for a person, in particular a child. By this, for example, a fixation target 38 moving farther away in the movie by being shown smaller and smaller to the eye 10, may be supported by actually moving the display 36 farther away from the eye 10.

The system 30" may further comprise a sound device 88 to play audio content to the person, in particular the child. Here, the content may comprise a melody for relaxing the mood of the person and hence avoid accommodation of the pupil. Further, the sound device 88 may play audio content corresponding to the video shown to the eye 10, for example the voice of figures or sound of objects shown in the video. This may help to maintain attention to the video. Probably, the sound device shall be positioned and emit the sound waves to the person from a direction that corresponds more or less to the viewing direction of the eye 10 to the display 36. By this, it is most likely avoided that the person, in particular the child, will become irritated by sounds coming from a different direction which might cause the eye 10 to move towards the direction where the sound comes from. However, this is undesired when measuring the wavefront 24 emanating from the eye 10.

Figure 6A:
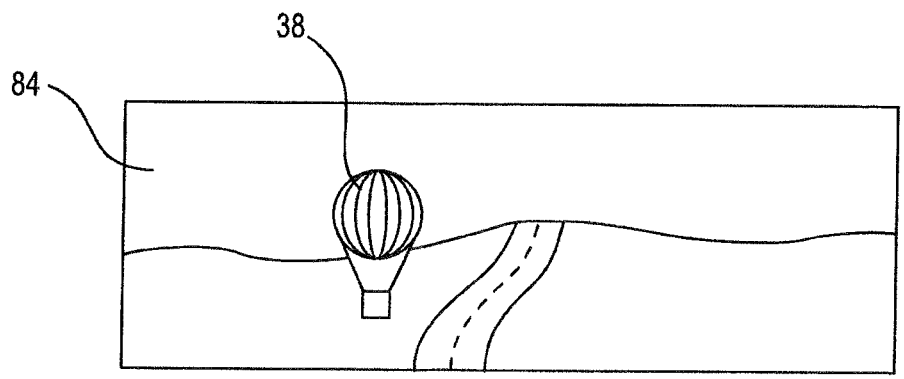
FIG. 6A shows a first image of a video.
Figure 6B:
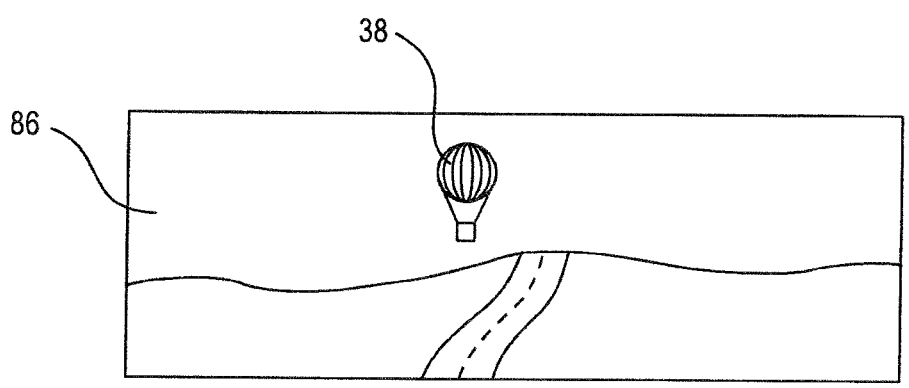
FIG. 6B shows a second image of a video.

FIGS. 6A and 6B show an example for a content that may be shown in the video on the display 36. FIG. 6A shows an image 84 with the fixation target 38 appearing quite "near" for the perception of the person, in particular the child. The fixation target 38 is shown to be a balloon flying in the air in front of a background of hills and a street curving into infinity at the horizon. For example, the person, in particular the child, may be told to fixate on stripes on the balloon.

FIG. 6B shows a further image 86 that may appear subsequently to the image shown in FIG. 6A. The image 86 shows the fixation target 38 "far away". By changing the size of the fixation target in its position, it appears to be farther away in the perception of the person, in particular the child. Hence, this helps to relax the eye of the child and to avoid accommodation, while keeping the attention of the child as its view follows the balloon disappearing into infinity. Hence, it may be provided that even a child, in particular even in an age from three years to ten years, can maintain its attention for a time period of approximately 20 to 30 seconds on the fixation target 38 without accommodation. This enables a high quality objective refraction with wavefront measurement techniques. Further, as already explained, while the fixation target 38 moves from a position indicated in FIG. 6A to a position indicated in FIG. 6B, an actual distance 82 of the display 36 shown in the images 84, 86 may be increased, so that the actual distance 82 between the eye 10 and the display 36 increases. This may further support avoiding accommodation of the eye.

Figure 7:
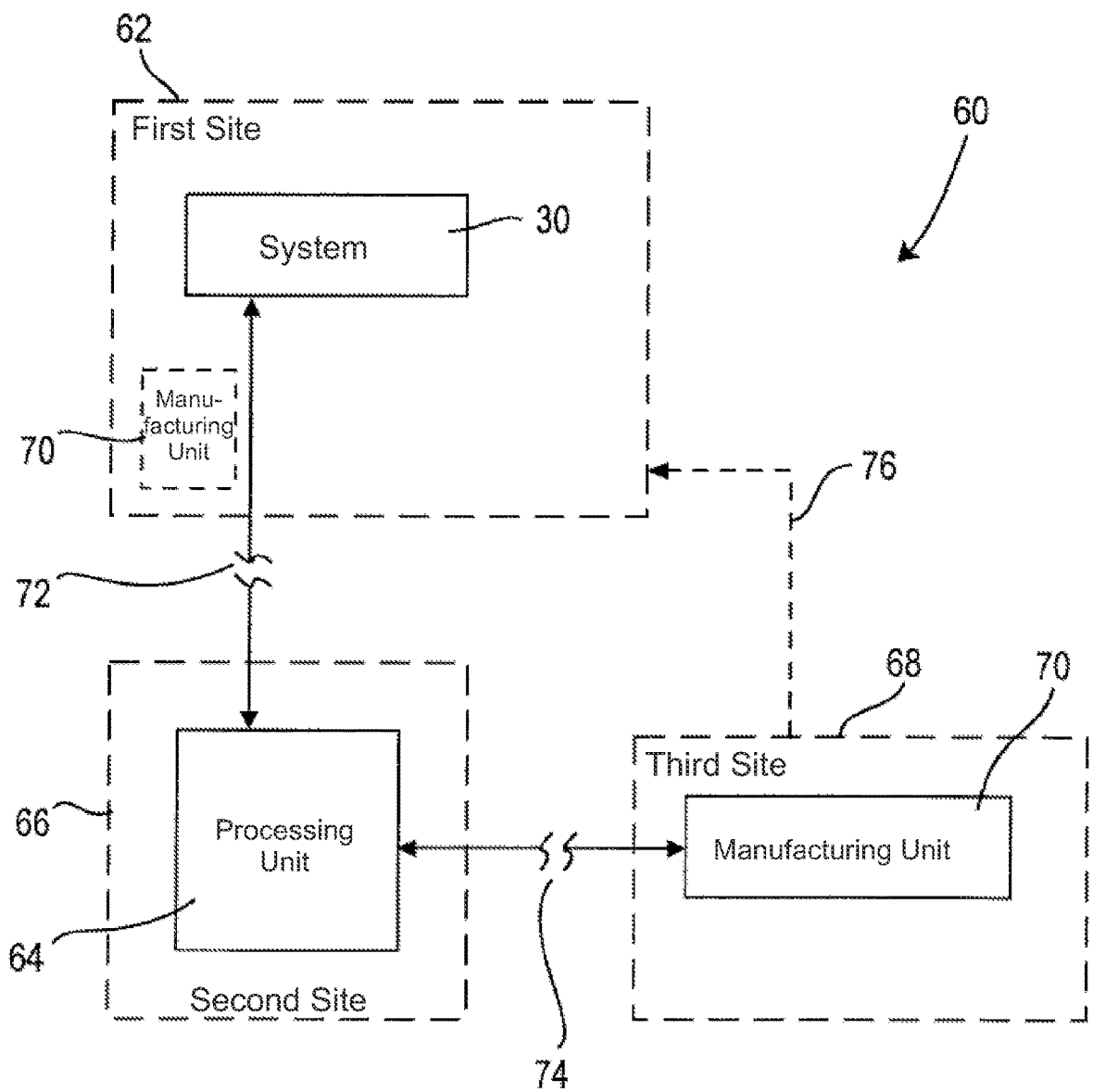
FIG. 7 shows an embodiment of an implementation of the system into a manufacturing system.

In FIG. 7, an embodiment of a manufacturing system 60 is shown. The system 30 for determining the refractive properties of the child's eye 10 may be located at a first site 62. A processing unit 64 may be located at a second site 66. The output device may be located at a third site 68 or may be also located at the first site 62. Further, a manufacturing unit 70 for manufacturing a visual aid may be present at either the third site 68 or the first site 62.

The first site 62, the second site 66 and the third site 68 are remote from each other. The first site 62 is connected with the second site 66 via a data network 72. The second site 66 and the third site 68 are connected via a data network 74. By this, it may be possible that refraction data provided via the aberrometer can be sent to the processing unit 64. Further, a subjective refraction, in particular a subjective corrective astigmatism, may also be sent to the processing unit 64, for example from the first site 62 or any other site. Further, for example, the determined eyeglass prescription may then be sent back to the first site, for example a spectacle shop, to be recognized by an ophthalmologist and provided to, for example, the possible wearer. Further, the eyeglass prescription determined can also be forwarded to a remote manufacturing unit to manufacture the respective visual aid. The manufacturing unit can be located at the first site 62. In this case, the data of the aberrometer is transmitted via connection 72 to the processing unit 64 at the second site 66 and then, the calculated eyeglass prescription is transferred back to the first site 62 and its possible manufacturing unit 70. Alternatively, from the second site 66, the determined eyeglass prescription can be transferred to a third site 68 with a possible manufacturing unit 70 to manufacture the visual aid. Last, it is possible that from this third site 68, the manufactured visual aid is then shipped to the first site 62 as indicated by the arrow 76.

Figure 8:
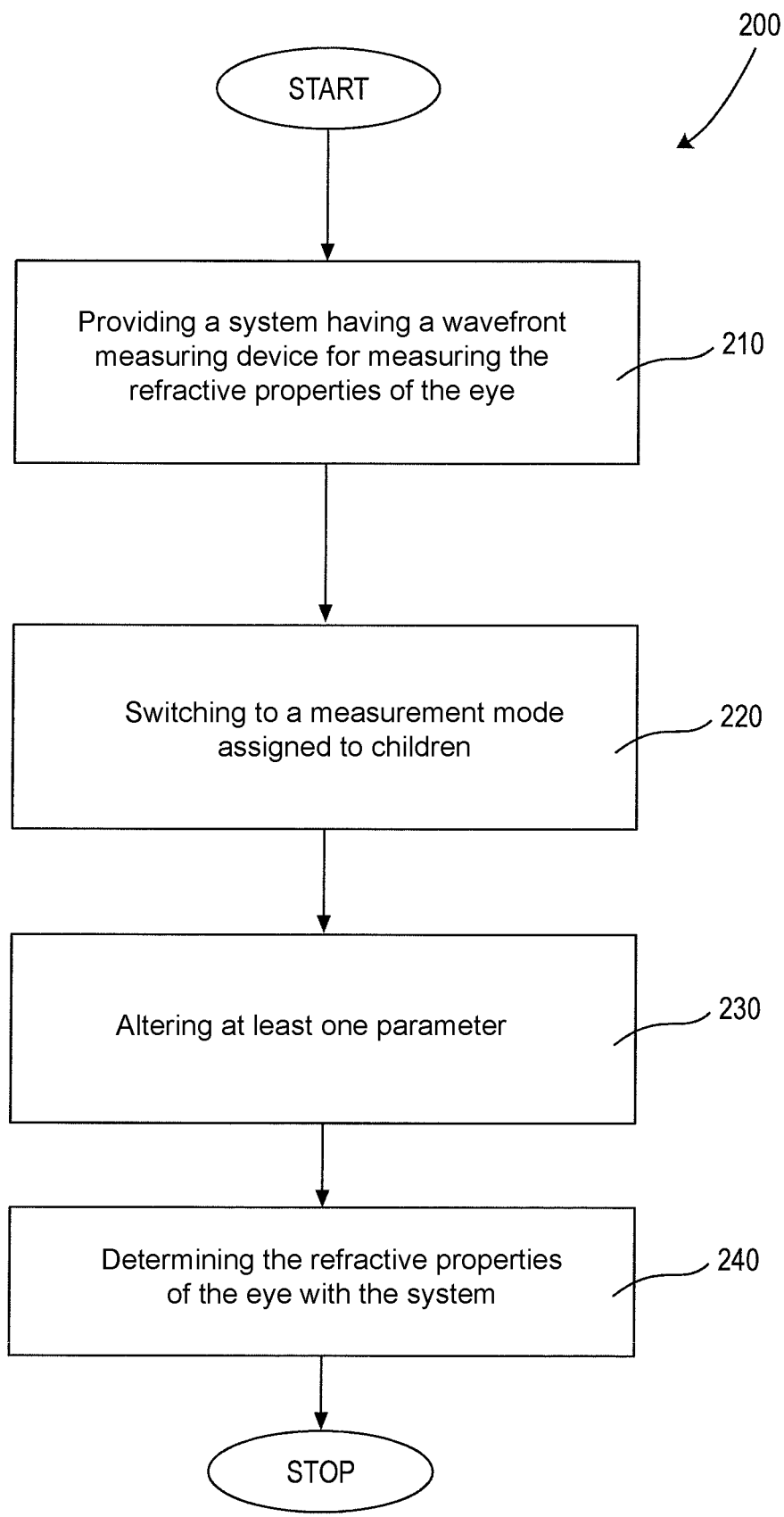
FIG. 8 shows a further embodiment of a method for determining the refractive properties of an eye.

FIG. 8 shows an embodiment of a method 200 for determining the refractive properties of the eye 10. After the method has started, a step 2010 is conducted in which a system 30 including a wavefront measurement device 32 for measuring the refractive properties of the eye 10 is provided. In step 220, this system is switched into one of at least one measurement mode assigned to children. This means that in step 230 at least one of a group consisting of a default pupillary distance, a default cornea vertex distance, a default position of the wavefront measurement device, a default direction of a measurement ray of the wavefront measurement device, a default position of a forehead and chin rest assembly of the system and the fixation target is altered. By this, the software and hardware properties of the system and, in particular, the wavefront measurement device, are being configured such that the system is specifically assigned for a wavefront measurement of the eye of a child. By this, the wavefront measurement result and, hence, a prescription for the child, may be acquired via objective refractive techniques only.

Hence, in step 240, the refractive properties of the eye are determined with the system 30.

Then, the method can end.

A further embodiment of the method designated with reference numeral. After start, a video comprising a fixation target to the eye 10 may be provided, wherein the video is a series of images shown with a frequency of at least 20 images per second. During the video being shown, there may be provided that the fixation target moves from a third perceived distance into a first perceived distance within the video provided with the eye. The first perceived distance shall be nearer to the eye in the perception of the person. Then, the fixation target 38 may move from the first perceived distance to a second perceived distance which is farther away from the eye in the perception of the person than the first perceived distance. Hence, in this step with the fixation target moving away from the person, it is likely that the eye 10 relaxes and accommodation may be avoided. Hence, the wavefront measurement may take place when the fixation target moves away from the person. This means, the actual and/or perceived distance of the fixation target increases, in particular towards infinity. Hence, it may be provided that a display is moved away from the eye by increasing its actual distance to the eye.

Figure 9:
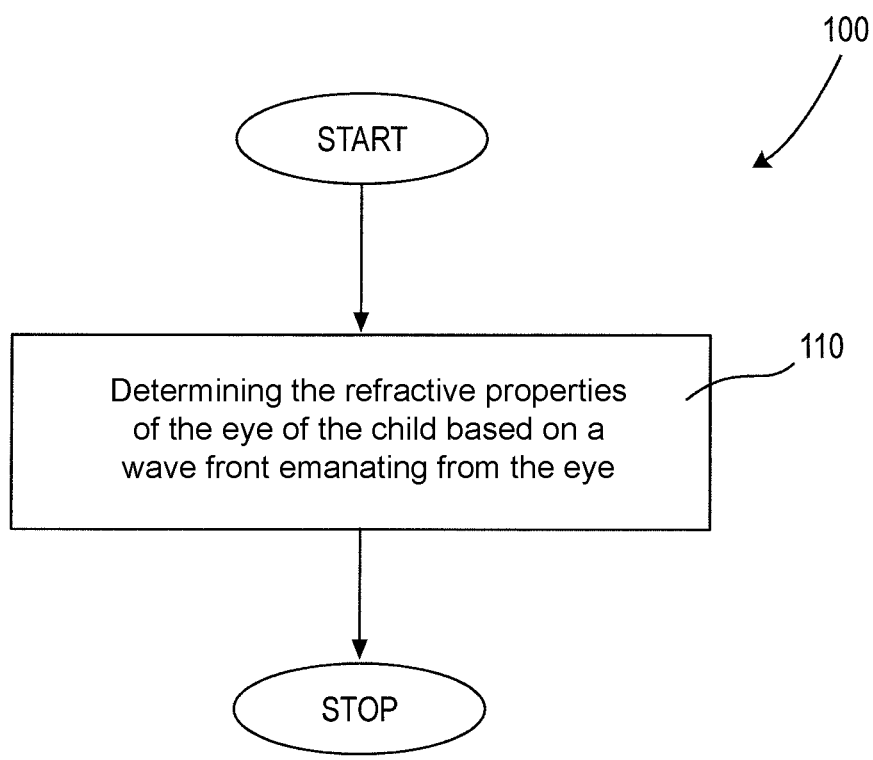
FIG. 9 shows an embodiment of a method for determining the refractive properties of an eye of a child.

FIG. 9 shows a method for determining the refractive properties of an eye of a child, which is generally designated with reference numeral 100.

After the message has started, a step 110 of determining the refractive properties of the eye of the child based on a wave front emanating from the eye is conducted. In particular, a wave front aberrometer is used, in particular based on the Shack-Hartmann-principle. Of course, the Tscherning principle ray tracing principle or any other type of wavefront aberrometer could be used also.

By this, as outlined above, the disadvantages of subjective refraction methods and retinoscopy when measuring the eye of a child can be overcome. It has been found that using a wave front measurement sensor can produce reliable results in practice when used for the automated objective refraction on children.

It may be preferred that the refractive properties of the eye of the child are determined only based on the wave front emanating from the eye and that the method 100 is finished after conducting step 110.

Figure 10:
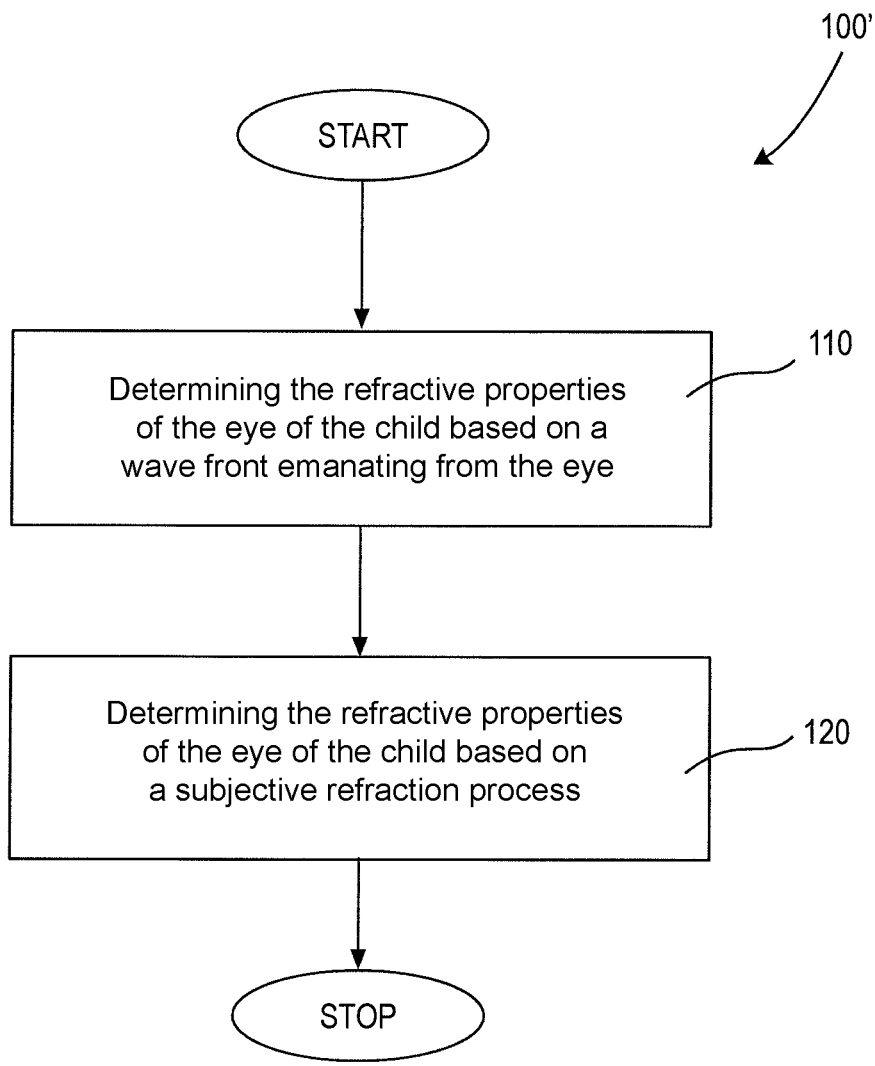
FIG. 10 shows a further embodiment of a method for determining the refractive properties of an eye of a child; and,
FIG. 11 shows an embodiment of a method for determining a spectacle lens design for a child.

FIG. 10 shows a further embodiment of the method 100.

As laid out above, it might be the case that only the step 110 is conducted to determine the refractive properties of the eye of a child. However, it may also be the case that a further step 120 is conducted wherein the refractive properties of the eye of the child are determined based on a subjective refraction process. In this subjective refraction process, the results obtained via the objective refraction process may be used as initial conditions for the subjective refraction. For example, the objective refraction processes step 110 may have been conducted and, based on the corresponding wave front results, a prescription for the child may have been found in sphere, cylinder and axis. These parameters of the prescription might then be used as starting conditions for the subjective refraction method. This provides for the advantage that the subjective refraction might be conducted significantly quicker as well as only slight amendments or refinements have to be found departing from the result found via the objective refraction in step 110.

Figure 11:
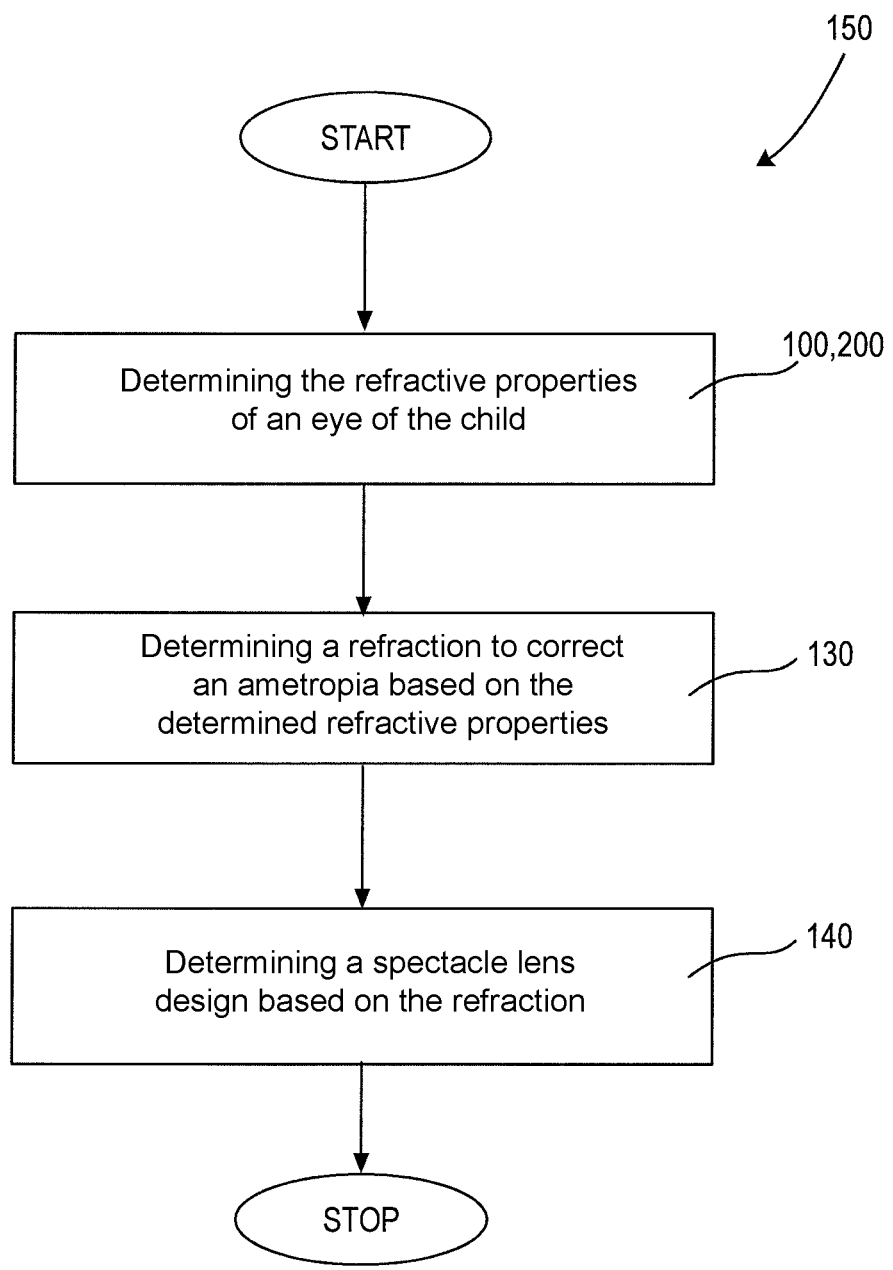

FIG. 11 shows an embodiment of a method for determining a spectacle lens design for a child. The method is generally designated with reference numeral 150.

After a method has started, at first, a method 100 as laid out initially is conducted to determine the refractive properties of an eye of the child.

Afterwards, a refraction to correct an ametropia based on the determined refractive properties is determined. For example, this may be a commonly known prescription in the form of sphere, cylinder and axis or M, J0 and J45. However, it is also possible that a higher order refraction in the form of an individually adapted lens surface might be found in this step 130.

Based on the refraction found in step 130, in a further step 140 it may then be determined a spectacle lens design based on the refraction. However, this lens design may be determined based on further individual parameters of the child, for example including the position of wear parameters such as pupillary distance, cornea vertex distance, pantoscopic angle and face frame angle. The refraction found in step 130 might be slightly adapted or optimized to find a lens design that fits the individual needs of the child and still complies with the refraction found in step 130 as good as possible. Such lens design methods are widely known to a person skilled in the art and are already explained in the documents cited in the introductory part of the description, for example.

In case the foregoing discussion refers to implementations for correcting up to second order aberrations, in general, the invention is not limited to second order aberrations. For example, in some embodiments, the methods can be expanded to allow refraction using higher order aberrations. Such a higher order refraction can then be used by the eyecare professional to specify an ophthalmic correction that includes higher order correction by altering the phase of the incident wavefront in the plane of the pupil according to the prescribed higher order aberration correction.

Furthermore, while the embodiments discussed above are in reference to eye glass visual aids, in general, the techniques can be applied to determining a prescription for contact lenses as well, which are to be considered as "visual aids".

It is understood that the foregoing description is that of the preferred embodiments of the invention and that various changes and modifications may be made thereto without departing from the spirit and scope of the invention as defined in the appended claims.

What is claimed is:

1. A system for determining the refractive properties of an eye while avoiding accommodation thereof, the system comprising:
   a wavefront measurement device for measuring the refractive properties of the eye, wherein the system is configured to have at least one measurement mode assigned to children,
   an input device configured to switch the system into said at least one measurement mode assigned to children, and wherein the system is further configured to select a fixation target based on a person's data, when the system is switched into said at least one measurement mode assigned to children,
   a display device for displaying the fixation target to the eye, wherein the display device is configured to show a video comprising the fixation target, wherein the video is a series of images shown with a frequency of at least 20 images per second, and wherein the system is, in said at least one measurement mode assigned to children and to avoid accommodation of the eye,
   the system being further configured to show the fixation target moving virtually from a first perceived distance from the eye to a second perceived distance therefrom during determination of the refractive properties of the eye, wherein the first perceived distance is less than the second perceived distance; and,
   the first perceived distance being in a range from and including 1 diopters to and including 4 diopters, and the second perceived distance being in a range from and including 0.5 diopters to and including 0 diopters.

2. A system for determining the refractive properties of an eye, the system comprising:

a wavefront measurement device for measuring the refractive properties of the eye, wherein the system is configured to have at least one measurement mode assigned to children, wherein the system has an input device configured to switch the system into said at least one measurement mode assigned to children, and wherein the system is further configured to alter at least one of the following defaults: a default pupillary distance, a default direction of a measurement ray of the wavefront measurement device and a default position of a forehead and chin rest assembly of the system, when the system is switched into said at least one measurement mode assigned to children;

said system being further configured to adjust the measurement ray based on said defaults so as to cause said measurement ray to closely match the actual position of the eye;

wherein the system further comprises an accommodation detection device and an alert device, wherein the accommodation detection device is a pupil size measurement device, and wherein the system is configured to provide an alert with the alert device in case an accommodation is detected by the accommodation detection device; and, wherein an accommodation of the pupil is detected and the alert provided by the alert device when a diameter of the pupil reduces its size below a threshold, wherein the threshold is set as 50% of a largest diameter of the pupil detected or as 70% of an initially detected diameter of the pupil.

3. The system according to claim 2, wherein the system is configured to move the forehead and chin rest assembly and/or the wavefront measurement device into an adjustment for adults to an adjustment assigned to children upon switching the system into the one of the at least one measurement mode assigned to children, wherein the adjustment is based on an average eye-to-chin distance, that is, a vertical distance between a measurement ray of the wavefront measurement device and a chinrest of the forehead and chin rest assembly, from and including 9.7 cm up to and including 10.7 cm.

4. The system according to claim 2, wherein the system is configured to alter the default pupillary distance upon switching the system into the measurement mode assigned to children, wherein the default pupillary distance is set to a value in a range from and including 45 mm to and including 55 mm.

5. The system according to claim 2, wherein the system is configured to alter a default cornea vertex distance upon switching the system into the measurement mode assigned to children, wherein the default cornea vertex distance is set to a value in a range from and including 10.5 mm to and including 11.5 mm.

6. The system according to claim 2, wherein the system is configured to alter a fixation target in the one of the at least one measurement mode assigned to children by at least one of a group consisting of choosing a type of the fixation target based on person's data, moving the fixation target on a display device of the system which display device is for displaying the fixation target and moving a display device of the system away from the eye which display device is for displaying the fixation target.

7. The system according to claim 2, wherein the system is configured to show a fixation target moving from a first perceived distance to a second perceived distance, wherein the first perceived distance is smaller than the second perceived distance, wherein the first perceived distance is in a range from and including 1 diopters to and including 4 diopters, and wherein the second perceived distance is in a range from and including 0.5 diopters to and including 0 diopters.

8. A method for determining the refractive properties of an eye while avoiding accommodation thereof, the method comprising the steps of:

providing a system including a wavefront measurement device for measuring the refractive properties of the eye;

switching the system into one of at least one measurement mode assigned to children;

altering a fixation target to the eye to avoid accommodation thereof, wherein the step of altering comprises showing the fixation target moving virtually from a first perceived distance from the eye to a second perceived distance therefrom during determination of the refractive properties of the eye, wherein the first perceived distance is less than the second perceived distance;

determining the refractive properties of the eye with the system, wherein the method further comprises showing a video comprising the fixation target, wherein the video is a series of images shown with a frequency of at least 20 images per second; and, the first perceived distance being in a range from and including 1 diopters to and including 4 diopters, and the second perceived distance being in a range from and including 0.5 diopters to and including 0 diopters.

9. A method for determining the refractive properties of an eye, the method comprising the steps of:

providing a system including a wavefront measurement device for measuring the refractive properties of the eye;

switching the system into one of at least one measurement mode assigned to children;

altering at least one of the following defaults: a default pupillary distance, a default direction of a measurement ray of the wavefront measurement device and a default position of a forehead and chin rest assembly of the system;

adjusting the measurement ray based on said defaults so as to cause said measurement ray to closely match the actual position of the eye;

determining the refractive properties of the eye with the system;

wherein the system further comprises an accommodation detection device and an alert device, wherein the accommodation detection device is a pupil size measurement device, and wherein the system is configured to provide an alert with the alert device in case an accommodation is detected by the accommodation detection device; and, wherein an accommodation of the pupil is detected and the alert provided by the alert device when a diameter of the pupil reduces its size below a threshold, wherein the threshold is set as 50% of a largest diameter of the pupil detected or as 70% of an initially detected diameter of the pupil.

10. The method according to claim 9, wherein the step of altering further comprises showing a fixation target moving from a first perceived distance to a second perceived distance, wherein the first perceived distance is smaller than the second perceived distance, wherein the first perceived distance is in a range from and including 1 diopters to and including 4 diopters, and wherein the second perceived distance is in a range from and including 0.5 diopters to and including 0 diopters.

11. A method for determining a spectacle lens configuration for a child, the method comprising the steps of:
   determining the refractive properties of an eye with the following steps:
   providing a system including a wavefront measurement device for measuring the refractive properties of the eye;
   switching the system into one of at least one measurement mode assigned to children;
   altering at least one of the following defaults: a default pupillary distance, a default direction of a measurement ray of the wavefront measurement device, a default position of a forehead and chin rest assembly of the system and a fixation target;
   adjusting the measurement ray based on said defaults so as to cause said measurement ray to closely match the actual position of the eye;
   determining the refractive properties of the eye with the system;
   determining a refraction to correct an ametropia based on the determined refractive properties;
   determining a spectacle lens configuration based on the refraction; and,
   wherein the system further comprises an accommodation detection device and an alert device, wherein the accommodation detection device is a pupil size measurement device, and wherein the system is configured to provide an alert with the alert device in case an accommodation is detected by the accommodation detection device.

12. The system of claim 2, wherein the pupil size measurement device interacts with the default pupillary distance and the adjustment of the measurement ray so that the pupils, during objective refraction via the wavefront measurement device, can be captured by the pupil size measurement device to provide an alert indicating accommodation during objective refraction via the wavefront measurement device.

13. The method of claim 9, wherein the pupil size measurement device interacts with the default pupillary distance and the adjustment of the measurement ray so that the pupils, during objective refraction via the wavefront measurement device, can be captured by the pupil size measurement device to provide an alert indicating accommodation during objective refraction via the wavefront measurement device.

14. The method of claim 11, wherein the pupil size measurement device interacts with the default pupillary distance and the adjustment of the measurement ray so that the pupils, during objective refraction via the wavefront measurement device, can be captured by the pupil size measurement device to provide an alert indicating accommodation during objective refraction via the wavefront measurement device.

15. The method of claim 11, wherein an accommodation of the pupil is detected and the alert provided by the alert device when a diameter of the pupil reduces its size below a threshold, wherein the threshold is set as 50% of a largest diameter of the pupil detected or as 70% of an initially detected diameter of the pupil.

16. The system according to claim 1, wherein said system defines a coordinate system X, Y, Z and further comprises:
   a housing for accommodating said wavefront measurement device therein;
   said wavefront measurement device being movable within said coordinate system X, Y, Z to be aligned toward the eye of said person;
   a head/chin assembly connected to said housing in spaced relationship to said wavefront measurement device;
   said head/chin assembly including a head rest for receiving the forehead of said person thereagainst and a chin rest whereupon the chin of said person is positioned during measurement of said refractive properties of the eye of said person; and,
   said head rest and said chin rest being movable relative to each other and relative to said wavefront measurement device in elevation in the X-direction of said coordinate system X, Y, Z.

17. The system according to claim 2, wherein said system defines a coordinate system X, Y, Z and further comprises:
   a housing for accommodating said wavefront measurement device therein;
   said wavefront measurement device being movable within said coordinate system X, Y, Z to be aligned toward the eye of said person;
   a head/chin assembly connected to said housing in spaced relationship to said wavefront measurement device;
   said head/chin assembly including a head rest for receiving the forehead of said person thereagainst and a chin rest whereupon the chin of said person is positioned during measurement of said refractive properties of the eye of said person; and,
   said head rest and said chin rest being movable relative to each other and relative to said wavefront measurement device in elevation in the X-direction of said coordinate system X, Y, Z.

18. The method according to claim 8, wherein said system defines a coordinate system X, Y, Z and further comprises:
   a housing for accommodating said wavefront measurement device therein;
   said wavefront measurement device being movable within said coordinate system X, Y, Z to be aligned toward the eye of said person;
   a head/chin assembly connected to said housing in spaced relationship to said wavefront measurement device;
   said head/chin assembly including a head rest for receiving the forehead of said person thereagainst and a chin rest whereupon the chin of said person is positioned during measurement of said refractive properties of the eye of said person; and,
   said head rest and said chin rest being movable relative to each other and relative to said wavefront measurement device in elevation in the X-direction of said coordinate system X, Y, Z.

19. The method according to claim 9, wherein said system defines a coordinate system X, Y, Z and further comprises:
   a housing for accommodating said wavefront measurement device therein;
   said wavefront measurement device being movable within said coordinate system X, Y, Z to be aligned toward the eye of said person;
   a head/chin assembly connected to said housing in spaced relationship to said wavefront measurement device;
   said head/chin assembly including a head rest for receiving the forehead of said person thereagainst and a chin rest whereupon the chin of said person is positioned during measurement of said refractive properties of the eye of said person; and, said head rest and said chin rest being movable relative to each other and relative to said wavefront measurement device in elevation in the X-direction of said coordinate system X, Y, Z.

20. The method according to claim 11, wherein said system defines a coordinate system X, Y, Z and further comprises:

a housing for accommodating said wavefront measurement device therein;

said wavefront measurement device being movable within said coordinate system X, Y, Z to be aligned toward the eye of said person;

a head/chin assembly connected to said housing in spaced relationship to said wavefront measurement device;

said head/chin assembly including a head rest for receiving the forehead of said person thereagainst and a chin rest whereupon the chin of said person is positioned during measurement of said refractive properties of the eye of said person; and, said head rest and said chin rest being movable relative to each other and relative to said wavefront measurement device in elevation in the X-direction of said coordinate system X, Y, Z.

21. The system according to claim 2, wherein said system is configured to alter all of said defaults when said system is switched into said at least one measuring mode assigned to children.

* * * * *